(12) United States Patent
Bird et al.

(10) Patent No.: US 6,994,869 B1
(45) Date of Patent: Feb. 7, 2006

(54) NASOGASTRIC ENTERAL FORMULATIONS (75) Inventors: Anthony R Bird, Adelaide (AU); Ian R Record, Adelaide (AU); David L Topping, Adelaide (AU)

(73) Assignee: The Commonwealth of Australia Commonwealth Scientific and Industrial Research Organization, Campbell ( * ) Notice: Subject to any disclaimer, the term of this patent is extended or adjusted under 35 U.S.C. 154(b) by 27 days.

(21) Appl. No.: 10/019,236

(22) PCT Filed: Jun. 30, 2000

(86) PCT No.: PCT/AU00/00792

§ 371 (c)(1),
(2), (4) Date: Apr. 11, 2002

(87) PCT Pub. No.: WO01/02016

PCT Pub. Date: Jan. 11, 2001

(30) Foreign Application Priority Data

Jul. 1, 1999 (AU) ................................. PQ1325

(51) Int. Cl.
*A61K 47/00* (2006.01)
*A61F 13/00* (2006.01)
(52) U.S. Cl. ................... 424/439; 424/434; 424/435
(58) Field of Classification Search ............ 424/400, 424/439, 489, 78.01
See application file for complete search history.

(56) References Cited

U.S. PATENT DOCUMENTS 5,723,446 A * 3/1998 Gray et al. ................. 514/21
5,840,860 A * 11/1998 Annison et al. ........... 536/1.11

FOREIGN PATENT DOCUMENTS

| EP | 451750 | 10/1991 |
| EP | 04510750 | 11/1996 |
| WO | WO 95/13801 | 5/1995 |
| WO | WO 9608261 A1 | 3/1996 |

OTHER PUBLICATIONS

Caderni et al., "Dietary Sucrose, Glucose, Fructose, and Starches Affect Colonic Functions in Rats," Nutrition and Cancer 1996, vol. 25, (No. 2), p. 179-184.

* cited by examiner

Primary Examiner—Thurman K. Page
Assistant Examiner—Isis Ghali
(74) Attorney, Agent, or Firm—Pillsbury Winthrop Shaw Pittman LLP (57) ABSTRACT

The present invention relates to a nasogastric formulation comprising an amino acid source, a carbohydrate source, a lipid source, and a fatty acid delivery agent wherein the fatty acid has a bond hydrolysable in the colon to deliver free fatty acids such as short chain fatty acid acetate without having an adverse affect on the capacity to pass through a tube for tube feeding.

53 Claims, 3 Drawing Sheets

NASOGASTRIC ENTERAL FORMULATIONS

This application is the National Phase of International Application PCT/AU00/00792 filed on Jun. 30, 2000 which designated the U.S. and was published under PCT article 21(2) in English.

This invention relates to an enteral formulation suitable for nasogastric administration.

BACKGROUND OF THE INVENTION

Humans and animals with certain conditions are either not able to or preferably do not take nutrition by conventional means. Such individuals can have sustenance administered parenterally such as by the use of a venous drip or enterally in the form of a specific liquid formulation delivered via intubation of the gastrointestinal tract. There are obvious disadvantages to administering sustenance parenterally in so far as the risk of trauma and infection is greatly increased and the rate at which material that can be administered is quite low. Moreover, certain types of material cannot be administered, for example, dietary fibre. Additionally there are risks in having a gastrointestinal system which is inactive for any extended length of time due to the absence of fibre and other poorly digestible materials as it can lead to atrophy and to a range of other histo-pathological changes to various regions and even in the shorter term diminishes the well being of an individual.

Food formulations for clinical conditions may be administered orally and that is the preferred route as it is the normal means of food ingestion. However, for certain specific conditions it is necessary or at least advantageous to administer the formulation enterally by a tube feeding systems such as by a nasogastric tube which delivers nutrients directly to the stomach.

The requirement for enteral feeding might be relatively short term for example where a patient or other individual is treated for a clinical condition where the patient may be unable to masticate, swallow or retain conventional forms of food. Alternatively the patient might be suffering from a condition that requires longer term treatment and enteral feeding might be administered at the residence of the patient for a prolonged period.

Enteral formulations, especially those, used for short periods are intended to replace the normal diet and so contain materials that reflect such diets, and these include nitrogenous material such as proteins, protein hydrolysates, peptides or amino acids, carbohydrates (whole or partially hydrolysed), lipids, vitamins and essential minerals are thus generally delivered as emulsions. No particular attention is given to maintaining an active colon for short term administration. It is recognised that an inactive large bowel in the longer term is undesirable, and commercial formulations which have "added fibre" are available, with a view of maintaining such activity. These formulations generally include a fermentable resistant starch or a fermentable non-starch carbohydrate that is resistant to digestion by human enzymes in the small bowel but is fermentable by the microflora in the large bowel. Cope et al. in U.S. Pat. No. 5,403,826 refer to the inclusion of dietary fibre to enteral formulations and exemplify the use of soy polysaccharides. These polysaccharides are in large part digested in the ileocaecal region and the proximal large bowel with none or only small amounts reaching the distal bowel (Annison. G. & Topping, D. L. (1994) Resistant starch: Chemical structure vs physiological function. Ann. Rev. Nutr. 14: 297–320) and the levels used in the formulation are quite low. Garleb et al. in U.S. Pat. No. 5,444,054 refers to the inclusion of dietary fibres and indigestible oligosaccharides so that SCFAs may be formed in the large bowel. Reference is also made to Green et al in U.S. Pat. No. 5,792,754 where a mixture of resistant fibre is provided which is claimed to provide for deliver a balance of activity alone the length of the gastrointestinal tract. The inventors believe that Cope, Garleb and Green, as well as commercially available formulations all suffer from the inability to deliver sufficient fibre to give an adequate elevation of short chain fatty acid (SCFA) levels in the colon.

Whilst the "fibre added" enteral formulations do go some way to alleviating the problems of a totally inactive gastrointestinal tract the degree of fermentation in the large bowel is simply not enough, particularly for patients that are fed enterally for extended periods. The relatively low level of delivery of fermentable fibre to the colon would be exacerbated where the medical treatment received by the patient has a marked impact on the microflora of the patient which therefore cannot or is inefficient at transforming fibre to SCFAs.

A consequence of long term enteral feeding is the manifestation of certain disorders of the caecum and colon due to at least in part inactivity and lack of nutrient. Such disorders might include atrophy and perforation of the bowel, the overgrowth of the normal microflora of the bowel by organisms which might potentially be pathogens and diarrhoea.

One primary restriction on the capacity to deliver is the quantity of fibre that can physically be delivered through a feeding tube such as a nasogastric tube rather than a reluctance to increase levels in enteric formulations. Nasogastric tubes are rather difficult to put into place and are unpleasant for the patient and thus the outside diameter of the tube is kept as small as possible with a consequent small internal diameter. Not only is the internal diameter a consideration but a pump or gravity is generally used to move the formulation through the tube. This means that the liquid within the tube is also under compression, so that any viscosity of the fluid is further compounded. The intrinsic viscosity of soluble fibre and protein in the partially or fully hydrolysed state can be high and thus poses a limitation. Some of the components of these formulation may be delivered as insoluble suspensions, however, the provision of insoluble suspensions is particularly undesirable for nasogastric application, because of the difficulties associated with sedimentation and phase separation and the difficulty of resorting to increased viscosities to alleviate settling out. The very much preferred approach to nasogastric application is to provide the solids in soluble form, which are supplied together with the fat component to form an emulsion.

A suggestion has been made in U.S. Pat. No. 5,919,822 by Cotter et al. in light of the restricted capacity of enteral formulation to include fibre provide SCFAs in enteral and parenteral formulations. Cotter et al do however not provide any data in terms of the efficacy of the delivery of SCFA, and it is believed that the predominance of the SCFA will be degraded before reaching the large bowel so that the formulation provides little benefit especially to the distal colon. The direct delivery of SCFA has only be achieved by an enema (Sheppach et al. (1992) Gastroenterology: 10: 51–56), or when complexed with a carrier (WO 95/13801).

It is believed by the inventors that the enteral formulations suggested to date do not supply an adequate amount of short chain fatty acids to the large bowel or at least do so inefficiently. Additionally in the event of a highly altered microflora of the large bowel which might result from chemotherapy or antibiotic treatment, the often quite complex transformation that are required to produce beneficial short chain fatty acids cannot be performed efficiently. Furthermore providing an enteral formulation that delivers benefit, in the form of elevated amounts of short chain fatty acids to the large bowel in a short time span has to the knowledge of the inventors not been done before.

For the purposes of this specification the word "comprising" means "including but not limited to", and the word "comprises" has a corresponding meaning. Also a reference within this specification to a document is not to be taken as an admission that the disclosure therein constitutes common general knowledge in Australia.

OBJECT OF THE INVENTION

It is an object of the present invention to provide an enteral formulation for nasogastric application which alleviates or reduces the disadvantages of the aforementioned problems, or at least provides the public with an choice.

SUMMARY OF THE INVENTION

WO 95/13801 in the name of the Commonwealth Scientific and Industrial Research Organisation discloses a means of enhancing the levels of short chain fatty acids delivered to the bowel to alleviate or overcome some disorders of the large bowel, however there is no indication that this material can be used in enteral tube feeding.

The present inventors now recognise that there are prospects of developing a workable enteral formulation suitable for nasogastric application which can reduce the problems associated with a physiologically inactive large bowel that are associated with enteral tube feeding.

It has been found that the fatty acid delivery agent can be delivered via an enteral tube to provide an elevated level of fatty acid in the colon. Additionally it has been found that the elevated level can be achieved remarkably quickly and without prior adaptation, and that at least one form of the fatty acid delivery agent has a stabilising effect on nasogastric formulations.

This invention provides for an enteral formulation suitable for use in nasogastric feeding, which includes a fatty acid delivery agent for enhanced delivery of fatty acids to the large bowel that have a beneficial effect in the large bowel. The fatty acids in the fatty acid delivery agent are covalently bonded to a carrier by a bond that is selectively cleavable in the large bowel to give free fatty acids. The fatty acid delivery agent is either soluble in water or the lipid phase of the prepared formulation or alternatively can be rendered stable by an emulsifying agent such as by packaging into liposomes. Most preferably the fatty acid delivery agent is soluble in water.

The fatty acids are selected as being of benefit to the health of the individual human or animal. The fatty acid might be one or more of the short chain fatty acids, which in the present context might be taken as having a carbon chain length of between 1 and 10. Preferably however the chain length is between 2 and 4, encompassing acetate, propionate and butyrate, from the literature these three SCFAs have the most evident health benefits. Alternatively a broader range of fatty acids are contemplated by this invention, which fatty acids play a role in benefits other than bowel health directly, and such fatty acids might be selected from the omega 3 fats (such as eicosapentaenoic acid.

EPA and docosahexenoic acid DHA, linolenic acid), omega 6 fats (such as linoleic acid), stearadonic acid, and conjugated fatty acids (such as conjugated linoleic acid). These fats may be given as triacylglycerols or partial glycerides or as phospholipids bonded to the carrier.

The carrier can be varied greatly and might include natural dietary fibre or non-digestible oligosaccharides or other biological molecules, alternatively a synthetic polymer might be used as the carrier. The carrier might thus be contemplated as being a faecal bulking agent. The invention however contemplates that the carrier will be capable of being used as an energy source for normal large bowel microflora. Generally it is anticipated that the carrier will preferably be a carbohydrate so that on cleavage of the fatty acid from the carrier, the carrier can then be used, firstly as a means for increasing the microflora of the large bowel, and secondly can be metabolised by at least a proportion of the microflora to form SCFA, to further enhance health benefits to the large bowel. More preferably the carrier is a starch and most preferably a resistant starch.

The degree of substitution is also of relevance in so far as many carriers that might be contemplated such as for example hydrolysed carbohydrates would have a tendency to exert osmotic effects that might, for example, give rise to diarrhoea. The latter condition is predisposed to some extent already by the adoption of a radically different diet and the absence of SCFA which facilitates fluid absorption. Whereas with suitable substitution the nature of a carrier molecule can be modified, so as to be a little more conducive to water retention by the large bowel. Additionally where the carrier is a natural carbohydrate such as a starch the substitution has a tendency to minimise gelatinisation, especially under heat treatment, thereby maintaining the resistance to digestion of the formulation by human enzymes in the small intestine after treatment for sterilisation. Additionally this will impact positively on the physical characteristics of the prepared formulation.

Examples of the bond between the fatty acid and the carrier are amide or ester bonds.

Other examples of fatty acid delivery agents can be determined by reference to WO 95/13801 which document is hereby incorporated by reference.

In one aspect the invention could be said to reside in an enteral formulation for nasogastric delivery including,
 a) an amino acid source
 b) a carbohydrate source,
 c) a lipid source, and
 d) a fatty acid delivery agent, being a fatty acid covalently bonded to a carrier molecule by a bond hydrolysable in the colon to thereby release the fatty acid.

In a preferred form the viscosity of the formulation in no greater than 40 centipoise (cP) when measured at 25° C. (using a Brookfield Dv-3 programmable rheometer with a cp40 cone) for ease of delivery, and more preferably the viscosity is no more than about 20 cP when measured at 25° C.

It is also preferred that the formulation is capable of being stored for at least 24 hours without forming a gel or precipitated or other non homogenous system that is not readily resuspended. Further formation of clumping or settling out is not preferred, because of the risk of not delivering the full formulation. The fibre component or fatty acid delivery agent is the component that will form the clumping or the gel and thus may result in the incomplete delivery of the formulation.

In a further aspect of the present invention the nasogastric elemental diet formulation include
 a) an amino acid source
 b) a sugar source
 c) a lipid source d) a mineral source
e) a vitamin source
f) and a fatty acid delivery agent as discussed and described herein.

The sources of a) to e) are generally conventional sources selected from those that do not interfere with nasogastric application, and do not adversely react with f) or react positively therewith. The sugar source may take the form of carbohydrates, which in part form the carrier of the fatty acid delivery agent where the carrier is a carbohydrate. Preferably however these are added separately so that metabolism and absorption can be achieved in the small bowel. The level of f) is sufficient to deliver a beneficial quantity of the combination of a bulking agent and fatty acid to the large bowel, and preferably the level of f) is in the range of greater than 5 grams per day, with the maximum being limited by viscosity constraints, however levels of up to 80 grams per day should be achievable by at least some embodiments, however more preferred is about 40 grams per day.

It is anticipated that the fatty acid delivery agent is made by taking a carrier and substituting fatty acids onto the carrier.

The daily dosage rate for a fatty acid delivery agent which takes the form of a resistant maize starch substituted by 2–4 carbon length SCFA at a degree of substitution of 0.25 could be in the range of 5 to 80 grams per day. This might be compared to a similar level of resistant starch requiring to be delivered at a rate in excess of 25 grams per day, to give the amount of SCFA required and demonstrated in WO95/13801, and by Sheppach et al. (1992) *Gastroenterology;* 10: 51–56). Given that the level of fluid delivery of enteral feeds is generally in the vicinity of 1 liter or up to 2 liters, the level of conventional carbohydrate required to be present (about 2.5% w/v), in addition to other constituents (such as those known to the skilled addressee) of the enteral feed is in excess of what would, by reason of viscosity, be readily deliverable through a nasogastric tube by a resistant starch. Beneficial effects of the fatty acid delivery agent may however be of value at a greater range of levels, and perhaps as low as 0.5% w/v of the final enteric formulation, the upper limit might be determined by solubility and thus might perhaps account for as much as 5% of the final enteric formulation as administered through the nasogastric tube.

Additionally the benefit of the present formulation is that the level of a predetermined fatty acid can be increased in the large bowel. Thus, for example, a butyrilated starch could be added to specifically increase the level of butyrate in the large bowel.

In the context of this specification the enteral composition is referred to as suitable for administration via a nasogastric tube, however the administration need not be limited thereto, but might also be administered via gastronomy and jejunostomy tubes, or may be orally consumed as a beverage.

A further aspect of the invention might be said to reside in a method of delivering a fatty delivery agent in a physiologically acceptable medium through a feeding tube to elevate the level of SCFA, the fatty acid delivery agent being a fatty acid covalently bonded to a carrier molecule by a bond hydrolysable in the colon to thereby release the fatty acid. This need not have all the normal nutritional requirements of an individual, but might be delivered quite independently of tube fed or other enteral formulations. This could be given as a separate feed, particularly where there is a wish to quickly boost the level of the relevant fatty acid in the large bowel, and it is anticipated that a formulation having quite high levels of fatty acid delivery agent could be delivered, perhaps as high as 30% or at least 25%. Certainly 20% of the exemplified fatty acid delivery agent could be made and it is anticipated that a higher level could be delivered. It will be understood however that generally it would be convenient to deliver the fatty acid delivery agent together with the other nutritional requirements of the individual concerned.

DETAILED DESCRIPTION OF THE EXEMPLIFIED EMBODIMENTS

EXAMPLES

Methods—Evaluation of Acetylated Starch in Nasogastric Feed Solutions in Rats—Effects on Large Bowel Fermentation A measured dose of the enteral feeding solution including acetylated starch was administered by gavage to rats to mimic the ingestion of food whilst avoiding the mouth. Then, at intervals of approximately two hours, caecal digesta was collected and SCFA levels determined subsequently. Other changes in the intracolonic environment, relevant to bowel health, were also monitored.

For each study, adult rats (Sprague Dawley, 250–350 g) were maintained on a standard basal colony diet (Joint Stock Ration available from Ridley Agri Products, Murray Bridge. South Australia) before being allocated to two or three treatments and three time-point slaughter groups. After depriving rats of food overnight, they were gavage-fed (4 ml) a slurry containing 1 g of either 3401C maize starch (Control, a high amylose starch available from Goodman Fielder, Melbourne, Australia) or acetylated starch (made according to Example 6). Gavage fed through an FG8 tube presterilised (available from Indoplas Pty Ltd Sydney). The FG8 tube was 40 cm in length with a 1 mm internal diameter and a 2 mm external diameter and positioned through the mouth and oesophagus to rest in the stomach. The solutions were forced through the FG8 tube using a syringe. At 2, 4 and 6 hours post-gavaging, rats were asphyxiated by $CO_2$ the abdominal cavity opened and the caecum excised. Caecal contents were expressed, weighed, diluted with a known quantity of internal SCFA standard (heptanoic (caproic) acid) and homogenised. After centrifugation (3000 rpm)

supernatant pH was measured and then an aliquot stored frozen to await analysis of SCFA. SCFA analysis was performed by the method described in Topping et al. (1993) *J Nutr.* 123: 133–143.

Example 1

Physical Properties of Various Starch Suspensions

All feeding solutions prepared by suspending 1 g of designated starch in 4 ml of water. This was not sterilised.

Acetylated Starch—thin slurry

3401C Control starch—thin slurry

Example 2

Pilot Study of Gavage Feeding with Digestible Starch and Acetylated Starch

This study was a pilot study using 2 female rats of about 400 g. The control starch 3401C was compared with acetylated starch produced by example 6. After overnight food deprivation rats were dosed and killed two hours later. The stomach of each of the rats were empty of contents, product was visible in small intestine.

Results

TABLE 1

| Starch | Caecal contents (g) | Ph |
|---|---|---|
| 3401C | 1.90 | 7.82 |
| Acetylated starch | 1.90 | 7.58 |

TABLE 2

| Starch | Acetate | Propionate | Butyrate |
|---|---|---|---|
| 3401C | 22.9 | 8.8 | 3.9 |
| Acetylated starch | 25.7 | 8.9 | 6.6 |

The measurement of the short chain fatty acids is a calculation of the total caecal content.

There is a numerically greater amount of butyrate present in the caecum of the rat fed Acetylated starch when compared to the rat fed 3401C control starch. There is no appreciable change in the amount of caecal content, pH of the caecum, or the levels of acetate or propionate.

Example 3

Time Trial of Gavage Feeding

This trial involved 6 male rats weighing about 330 g. The starches used were 3401C control starch or acetylated starch made in accordance with the method set out in example 6. Feed preparation of 1.25 g of starch were added to 5 ml water and used fresh. Each dosage was 4 ml.

Rats dosed with various starches and killed 2, 4 and 6 hours later. The stomachs of each of the rats was empty of contents but products visible in small intestine. The contents of the caeca were processed as set out in the description of the methods.

Results

TABLE 3

| Starch | Caecal contents (g) | Ph |
|---|---|---|
| 3401C - 2 h | 2.22 | 7.62 |
| 3401C - 4 h | 1.65 | 7.72 |
| 3401C - 6 h | 2.55 | 7.27 |
| Acetylated starch - 2 h | 1.60 | 7.72 |
| Acetylated starch - 4 h | 1.80 | 6.97 |
| Acetylated starch - 6 h | 2.24 | 6.14 |

TABLE 4

| Starch | Acetate | Propionate | Butyrate |
|---|---|---|---|
| 3401C - 2 h | 21.1 | 6.7 | 4.7 |
| 3401C - 4 h | 22.0 | 7.6 | 4.1 |
| 3401C - 6 h | 31.4 | 10.9 | 6.5 |
| Acetylated starch - 2 h | 24.6 | 7.7 | 4.5 |
| Acetylated starch - 4 h | 30.5 | 8.0 | 6.4 |
| Acetylated starch - 6 h | 34.5 | 10.1 | 11.4 |

Figure 1:
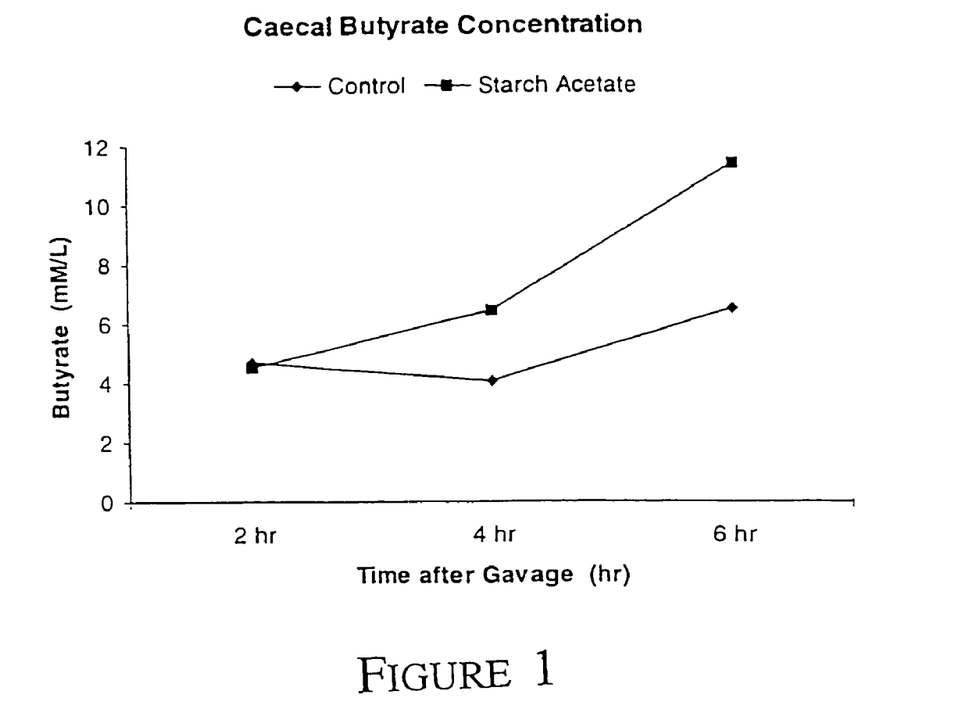
FIG. 1 Is a plot of the results of example 3 wherein the butyrate concentration of the caecum of a rat was determined at time points 2, 4 and 6 hours after ingestion of starch acetate ■ or a control fed starch 3401C ♦, FIG. 2 Is a plot of the results of examples 3 and 4 wherein the pool of acetate of the caecum of a rat was determined at time points 2, 4 and 6 hours after ingestion of starch acetate ■ or a control fed starch 3401C ♦, FIG. 3 Is a plot of the results of examples 3 and 4 wherein the pool of propionate of the caecum of a rat was determined at time points 2, 4 and 6 hours after ingestion of starch acetate ■ or a control fed starch 3401C ♦, FIG. 4 Is a plot of the results of examples 3 and 4 wherein the pool of butyrate of the caecum of a rat was determined at time points 2, 4 and 6 hours after ingestion of starch acetate ■ or a control fed starch 3401C ♦, and FIG. 5 Is a plot of the results of examples 3 and 4 wherein the pool of total short chain fatty acids of the caecum of a rat was determined at time points 2, 4 and 6 hours after ingestion of starch acetate ■ or a control fed starch 3401C ♦.
Figure 2:
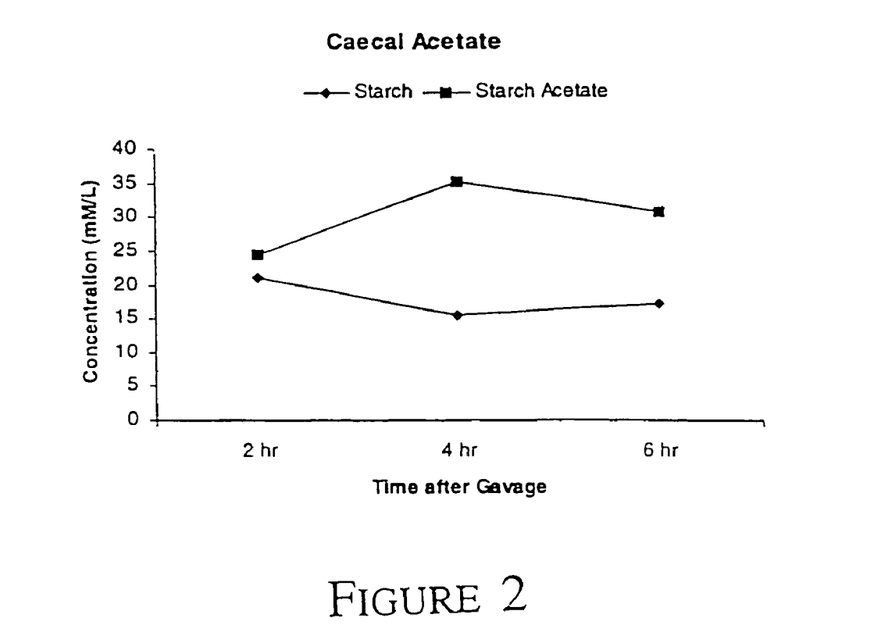
Figure 3:
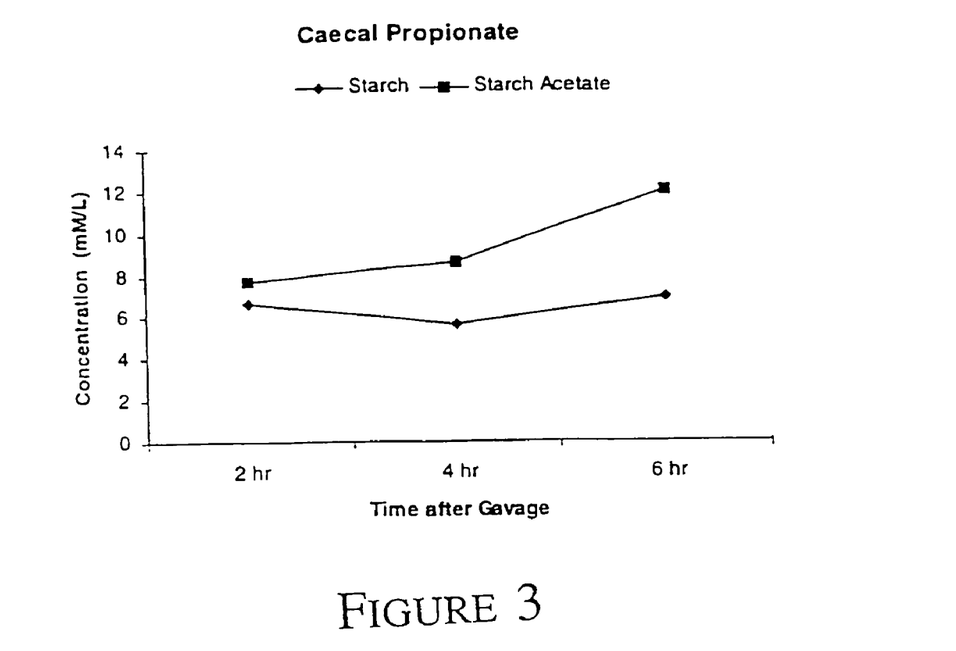
Figure 4:
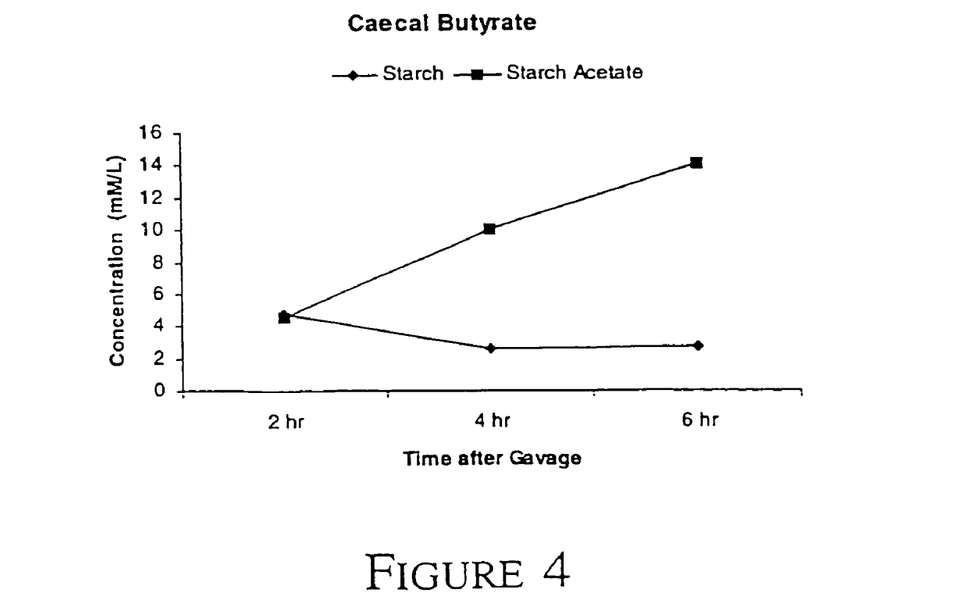
Figure 5:
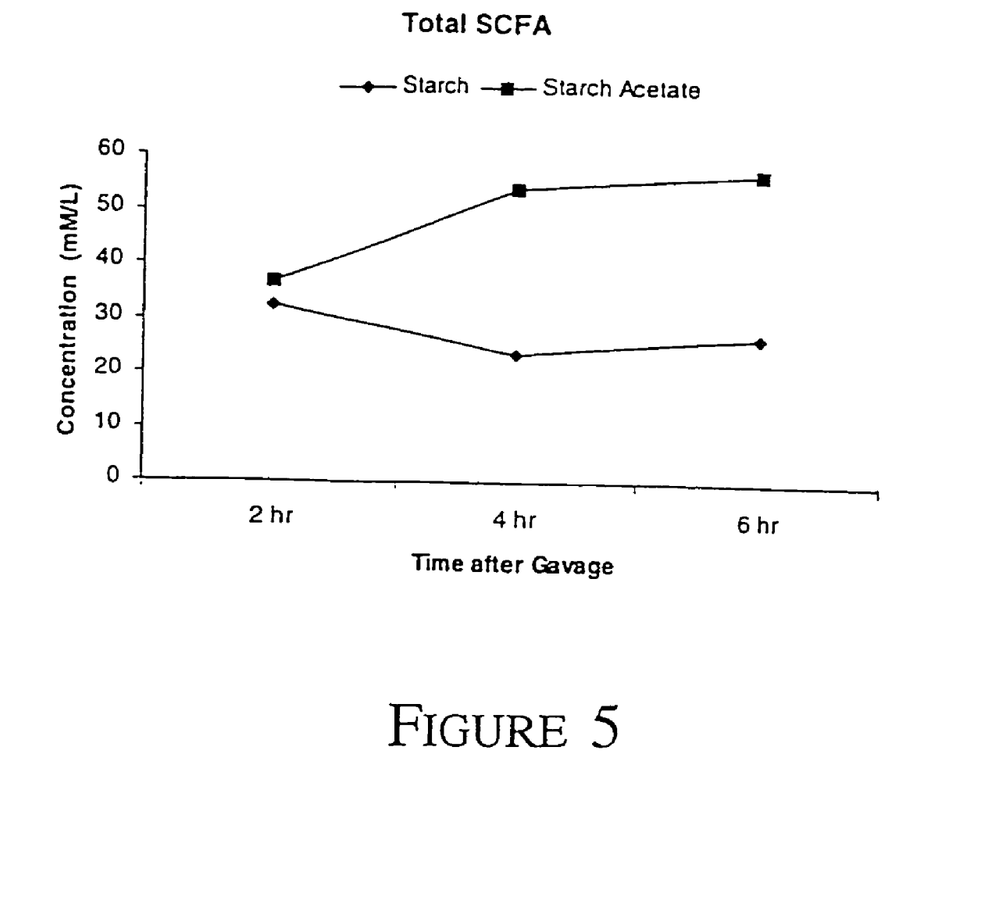

It can be seen that there is a numerical difference in the level of butryate found in the caeca of rats both after 4 hours and 6 hours after gavage feeding. FIG. 1 is a plot of the caecal butyrate concentration.

Example 4

Time Course Effect of Acetylated Starch

This trial involved 15 male rats weighing about 370 g. The starches used were 3401C control starch or acetylated starch made in accordance with the method set out in example 6. Feed preparation of 1.25 g of starch were added to 5 ml water and used fresh. Each dosage was 4 ml. a control with only water (n=1) was also included.

Rats dosed with various starches and killed 4, 6 and 8 hours later. The stomach of each of the rats was empty of contents but product was visible in small intestine. The contents of the caeca were processed as set out in the description of the methods.

Results

TABLE 5

| Starch | Time | Acetate | Propionate | Butyrate | Total | Caecal Content | pH |
|---|---|---|---|---|---|---|---|
| Water Control | | | | | | | |
| | 4 hr | 9.1 | 4.1 | 0.8 | 14.0 | 2.58 | 7.52 |
| | 6 hr | 22.9 | 8.1 | 1.1 | 32.1 | 2.38 | 7.44 |
| | 8 hr | 21.1 | 7.3 | 0.9 | 29.3 | 1.25 | 7.48 |
| 3401C Starch | | | | | | | |
| | 4 hr | 8.5 | 4.8 | 0.8 | 14.1 | 1.6 | 7.63 |
| | 4 hr | 16.2 | 4.4 | 2.9 | 23.5 | 1.5 | 7.83 |
| | 6 hr | 6.4 | 3 | 0.5 | 9.9 | 1.42 | 7.64 |
| | 6 hr | 13.9 | 6.9 | 1.1 | 21.9 | 1.91 | 7.40 |
| | 8 hr | 31.5 | 12.2 | 1.2 | 44.9 | 2.64 | 7.22 |
| | 8 hr | 22.0 | 8.2 | 1.0 | 31.2 | 1.54 | 7.44 |
| Acetylated Starch | | | | | | | |
| | 4 hr | 51.6 | 11.0 | 13.9 | 76.5 | 3.47 | 6.46 |
| | 4 hr | 23.6 | 6.9 | 9.7 | 40.2 | 2.53 | 6.43 |
| | 6 hr | 40.8 | 13.6 | 14.8 | 69.2 | 2.76 | 6.36 |

TABLE 5-continued

| Starch | Time | Acetate | Propionate | Butyrate | Total | Caecal Content | pH |
|---|---|---|---|---|---|---|---|
| | 6 hr | 17.5 | 12.2 | 15.8 | 45.5 | 4.85 | 6.40 |
| | 8 hr | 30.3 | 9.4 | 12.3 | 52.0 | 2.36 | 6.35 |
| | 8 hr | 43.6 | 16.1 | 13.3 | 73.0 | 2.94 | 6.45 |

Caecal ammonia was also measured in rats killed at 6 hours and there is a significant difference with the control starch 3401C. Control measured 10.1 mM as opposed to the acetylated starch measured 4.1 mM. FIGS. 2, 3, 4, and 5 are composite figures using data from example 3 and 4, showing the calculated amount of caecal acetate, caecal propionate, caecal butyrate and total SCFA (combination of acetate, propionate and butyrate) times 4 and 6 hours are combined and time 8 is omitted. These data show that in all cases there is an increase in the amount of the SCFA concerned. Using time pooled data it can be seen that all values are significant (see table 6 below).

Of interest is to note the lack of appreciable difference between the water controls and the starch control. There is considerable variation in the numerical values of each sample.

The data in the table below represents the pooled data from the 3401C control and the rats fed acetylated starch.

TABLE 6

Concentration of individual and total SCFA in the caecum of rate gavaged with Acetylated starch A (Example 4)

| | mmol/L | | | |
|---|---|---|---|---|
| 18 | 18 | Propionate | Butyrate | Total |
| Control | 16.4 | 6.6 | 1.3 | 24.3 |
| Starch Acetate | 34.6 | 11.5 | 13.3 | 59.4 |
| P value | 0.039 | 0.023 | 0.001 | 0.069 |

Values are least square means of 6 male rats per group. Caecal contents were collected at 4, 6, and 8 hour post gavaging. As there were no significant (P > 0.05) time effects values were averaged across the three sampling time points.

Example 5

Time Course Effect of Acetylated Starch

This trial involved 36 male rats weighing about 330 g. The starches used were 3401C control starch or acetylated starch made in accordance with the method set out in Example 6. Feed preparation of 1.25 g of starch were added to 5 ml water and used fresh. Each dosage was 4 ml, a control with only water (n=1) was also included.

Rats dosed with various starches and killed 2.4 and 6 hours later. The stomachs of each of the rats was empty of contents but products visible in small intestine. The contents of the caeca were processed as in example 2.

TABLE 7

| Control Starch | Caecal Content (g) | pH | Time (hours) | Starch acetate | Caecal Content (g) | pH |
|---|---|---|---|---|---|---|
| 1 | 1.42 | 7.10 | 2 | 1 | 1.91 | 7.51 |
| 2 | 1.27 | 7.29 | | 2 | 3.01 | 7.25 |
| 3 | 0.83 | 7.50 | | 3 | 0.56 | 7.20 |
| 4 | 0.42 | 6.97 | | 4 | 2.26 | 7.12 |
| 5 | 0.40 | 7.53 | | 5 | 1.89 | 7.25 |
| 6 | 1.12 | 7.23 | | 6 | 1.51 | 6.85 |
| Mean | 0.91 | 7.27 | | Mean | 1.86 | 7.20 |
| SD | 0.43 | 0.22 | | SD | 0.81 | 0.21 |
| 7 | 2.36 | 7.30 | 4 | 7 | 0.45 | 6.27 |
| 8 | 1.12 | 7.08 | | 8 | 1.22 | 6.82 |
| 9 | 1.70 | 7.27 | | 9 | 1.48 | 6.63 |
| 10 | 2.78 | 7.07 | | 10 | 1.34 | 6.94 |
| 11 | 2.95 | 6.74 | | 11 | 2.99 | 6.60 |
| 12 | 0.14 | 7.26 | | 12 | 1.85 | 6.12 |
| Mean | 1.84 | 7.12 | | Mean | 1.56 | 6.56 |
| SD | 1.08 | 0.21 | | SD | 0.84 | 0.32 |
| 13 | 1.13 | 6.89 | 6 | 13 | 2.64 | 5.93 |
| 14 | 0.32 | 7.03 | | 14 | 1.70 | 5.91 |
| 15 | 1.73 | 7.18 | | 15 | 0.52 | 5.78 |
| 16 | 0.66 | 7.06 | | 16 | 2.54 | 6.00 |
| 17 | 1.13 | 7.30 | | 17 | 2.72 | 6.01 |
| 18 | 2.33 | 6.63 | | 18 | 3.16 | 6.36 |
| Mean | 1.22 | 7.02 | | Mean | 2.21 | 6.00 |
| SD | 0.73 | 0.23 | | SD | 0.96 | 0.20 |

TABLE 8

| | Caecal SCFA pool (mM) | | | | | | | | | |
|---|---|---|---|---|---|---|---|---|---|---|
| Control Starch | Acetate | Propionate | Butyrate | Total | Time (h) | Starch Acetate | Acetate | Propionate | Butyrate | Total |
| 1 | 48.5 | 13.1 | 5.6 | 67.1 | 2 | 1 | 22.8 | 11.6 | 6.9 | 41.3 |
| 2 | 24.0 | 11.1 | 4.8 | 39.8 | | 2 | 19.5 | 14.0 | 6.5 | 40.0 |
| 3 | 4.2 | 3.1 | 1.9 | 9.1 | | 3 | 15.7 | 4.7 | 3.0 | 23.4 |
| 4 | 12.6 | 3.7 | 2.0 | 18.3 | | 4 | 70.3 | 23.1 | 12.8 | 106.3 |
| 5 | 10.9 | 3.6 | 1.5 | 16.0 | | 5 | 43.4 | 15.0 | 8.5 | 66.8 |

TABLE 8-continued

Caecal SCFA pool (mM)

| Control Starch | Acetate | Propionate | Butyrate | Total | Time (h) | Starch Acetate | Acetate | Propionate | Butyrate | Total |
|---|---|---|---|---|---|---|---|---|---|---|
| 6 | 16.0 | 6.5 | 2.1 | 24.6 | | 6 | 46.5 | 15.9 | 9.1 | 71.5 |
| Mean | 19.4 | 6.8 | 3.0 | 29.2 | | Mean | 36.4 | 14.1 | 7.8 | 58.2 |
| 7 | 68.2 | 23.0 | 12.5 | 103.7 | 4 | 7 | 5.8 | 1.5 | 1.3 | 8.7 |
| 8 | 33.0 | 9.5 | 4.7 | 47.1 | | 8 | 24.2 | 5.0 | 5.3 | 34.5 |
| 9 | 13.6 | 6.7 | 2.9 | 23.1 | | 9 | 45.1 | 8.5 | 7.9 | 61.6 |
| 10 | 75.2 | 29.4 | 14.7 | 119.2 | | 10 | 25.6 | 8.1 | 4.1 | 37.8 |
| 11 | 63.2 | 18.2 | 23.6 | 105.0 | | 11 | 66.5 | 19.1 | 20.3 | 106.0 |
| 12 | 2.9 | 1.0 | 0.7 | 4.6 | | 12 | 53.6 | 13.5 | 13.0 | 80.1 |
| Mean | 42.7 | 14.6 | 9.9 | 67.1 | | Mean | 36.8 | 9.3 | 8.7 | 54.8 |
| 13 | 31.6 | 8.6 | 5.5 | 45.7 | 6 | 13 | 59.1 | 16.3 | 16.9 | 92.3 |
| 14 | 10.0 | 2.5 | 2.5 | 15.0 | | 14 | 35.9 | 12.4 | 8.6 | 56.8 |
| 15 | 38.9 | 13.0 | 7.3 | 59.2 | | 15 | 16.8 | 3.7 | 2.7 | 23.2 |
| 16 | 20.2 | 5.9 | 3.2 | 29.3 | | 16 | 33.5 | 8.1 | 7.1 | 48.8 |
| 17 | 30.5 | 8.0 | 4.4 | 42.8 | | 17 | 109.5 | 31.6 | 19.1 | 160.2 |
| 18 | 51.8 | 15.3 | 11.6 | 78.7 | | 18 | 119.1 | 30.8 | 30.3 | 180.2 |
| Mean | 30.5 | 8.9 | 5.8 | 45.1 | | Mean | 62.3 | 17.2 | 14.1 | 93.6 |

There are no statistically significant time effects. Examination of data show that SCFA was highest at 6 hours in rats fed acetylated starch, but examination of table 7 shows a continuous decline in pH. This suggests that SCFA generation and attendant change of pH was occurring before a significant difference in actual amount of SCFA was measured. The 4 hour values are out of line with that observation and those of the earlier data and for that reason the 2 hour and 6 hour time points only were analysed.

TABLE 9

Caecal pools of individual and total SCFA in rats gavaged with acetylated starch in Example 5, 2 and 6 hour time point only

| | mmol/L | | | |
|---|---|---|---|---|
| Dietary Group | Acetate | Propionate | Butyrate | Total |
| Control | 24.9 | 7.9 | 4.4 | 37.1 |
| Starch Acetate | 49.3 | 15.6 | 11.0 | 75.9 |
| P value | 0.033 | 0.017 | 0.009 | 0.022 |

Values are least squares means of 12 male rats per group. Caecal contents collected at 2 and 6 hours post gavaging. Data for 4 hour collection excluded. As there were no significant (P > 0.05) time effects vales were averaged across the two sampling time points.

It can thus be seen that there is a statistically significant increase in the amount of the individual SCFA present in the caeca of the rats fed with acetylated starch when compared with the caeca of rats fed control starch.

Discussion

It can be seen that significant levels of acetylated starch can be introduced into the bowel of the experimental animals and further that these result in significant increases in the amounts of SCFA in the caeca of these animals. These SCFA are known to have a significant effect on bowel health, and in particular butyrate is implicated in regeneration and repair of colonocytes.

An important aspect of these results is the extremely short time span over which the physiological increase in the amount of SCFA is elicited without prior adaptation of the animals. The changes occur in less than two hours, the lower time limit is not known. The significance of that is that there is then provided a means of very rapid delivery of SCFA to the bowel using an enteral feeding method. It is speculated that there is no need for the resident microflora to significantly adapt to the new source of SCFA. This has implications for individuals who could benefit from such a rapid and effective delivery mode of SCFA. Given the ubiquity of the esterases it is likely that the presence of any bacteria in the large bowel will be able to cleave the SCFA from the carrier, and therefore individuals with microflora that might be compromised by reason of treatments such as antibiotics or chemotherapy will also be readily able to enable delivery of the SCFA.

This has particular significance to treatment where such delivery is desirable. In instances where a patient undergoes surgery, for example a colonic resection, and requires optimal conditions for repair of the bowel, a nasogastric formulation for delivery of SCFA to the large bowel is highly desirable. Thus the formulation may be useful not only for the long term health where a patient might suffer as a result of a lack of activity in the large bowel, but also for the short term such as in enteral feed formulations used for example in intensive care units of hospitals.

Example 6

Preparation of Acetylated High Amylose Maize Starch

The following chemicals and materials were used to prepare the acetylated HA (High Amylose) maize starch:

TABLE 10

| Reagents | |
|---|---|
| HA maize starch [Hi-maize ™] (Goodman Fielder Australia). | 350 kg. |
| Water. | 560 L. |
| Acetic anhydride. | 24.5 L. |
| Hydrogen peroxide [100 vol.] | 1.47 L. |
| Sodium hydroxide [0.65M]. | As required. |
| Hydrochloric acid [10M]. | As required. |

The method employed to acetylate the HA maize starch utilized the following protocol;
1. Measurement of the required quantity of water into the reaction vessel.
2. Addition of the starch.
3. Adjustment of the pH of the slurry to pH 8.01±0.1 using sodium hydroxide solution.
4. Addition of the hydrogen peroxide.

5. Agitation of the slurry for 45 mins.
6. Addition of acetic anhydride while simultaneously adding sodium hydroxide solution.

The pH was maintained in the range 8.0 to 8.5. The reaction was completed in less than 30 mins.

7. Permit the slurry to mix for 30 mins. The pH was maintained in the range 8.0 to 8.5.
8. The pH was adjusted to 5.0 to 6.5 with hydrochloric acid.
9. The starch was washed, dried and ground [to pass through a 212 Micron screen].
10. The recovered starch had a degree of substitution of 0.25

Example 7

Nasogastric Feeding Mixtures—Physical Properties

Three mixtures were prepared using acetylated starch at 1%, 2.5% and 5% (g/mL) to a final preparation constituted as set out below

TABLE 11

| Ingredients | |
|---|---|
| Ingredient | g per L |
| Casein | 46 |
| Oil* | 41 |
| Starch# | — |
| Sucrose | 33 |
| Vitamin mix | 0.4 |
| Mineral mix | 4.6 |
| Water | 821 |

Acetylated Starch - 1, 2.5 and 5%
*Lecithin was added as 3% of the oil content

The acetylated starch was suspended in 100 to 150 mL of RO (Reverse Osmosis) water and then treated at 100° C. for 50 minutes to gelatinise.

The 11.5 g of casein required for a 250 mL mixture was taken up in an individual amount of 50 mL of RO water that had 30 drops of 10 mM sodium hydroxide added to lower the pH. The resulting casein gel was added to the warm gelatinised starch solution, followed by the oil, lecithin, mineral/vitamin mix and dissolved sucrose. The volume was adjusted to 250 mL and mixed by shaking.

Viscosities were measured using a Brookfield DV-3 programmable rheometer with a cp40 cone.

Flow characteristics were measured by allowing the mixtures to flow under gravity from a Flexitainer (500 mL Enteral Nutrition Container) through an enteral feeding set (1.5 m long, 3.5 mm bore) connected to a Flexiflow feeding tube (#10F 114 cm long with an end outlet of 2 mm internal diameter plus two side outlet holes of similar diameter). The flexitainer was 2.6 m high and the feeding tube outlet was 0.9 m above the floor to mimic feeding a patient in the sitting position.

TABLE 12

Viscosity measurement of formulations including acetylated starch

| Mixture | Viscosity cP at 25° C. | Time (Min) |
|---|---|---|
| 1.0% | 7.2 | 7 min 40 seconds |
| 2.5% | 13.2 | 12 min 30 seconds |
| 5.0% | 60.8 | † |
| Nutrison ™ | 19.3 | 20 min 25 seconds |

†Would not flow through the first tube (3.5 m)
*Nutrison energy: from Nutricia, Zoetermeer, Holland.

It is anticipated that a solution with a viscosity of about 40cP and at a rate of shear of 120 sec$^{-1}$ at 25° C. as determined above will be able to be used through a feeding tube. It is estimated that the limit of the acetylated starch preparation that one could workably deliver using the formulation currently devised is about 4%, however it is anticipated that using different formulations that the level might be raised to 5%.

A further test was conducted in relation to 1% solutions of Hi Maize™ and the acetylated starch preparation made in accordance with Example 6 added to the formulation set out in table 11. These were readily solubilised and boiled. On storing overnight at 4° C. the HiMaize™ preparation formed a hard gel on the bottom of the storage vessel, and could not readily be dispersed by agitation. It is thought that this hard gel may be formed by the starch which is of a particulate nature, being converted to a retrograde state. Many nasogastric formulations have a high cation content and appear to have exacerbated gel formation of this nasogastric preparation, whereas in the case of the substituted version of the starch no such settling out was seen. In fact the acetylated starch had the properties of a stabiliser of the emulsion formed by the nasogastric formulation because it kept the phases from separating, and any particulates from settling.

The capacity to deliver a solution of 4% acetylated starch as a tube delivered enteral formulation give quite a high capacity to deliver nutrients. An usual maximum delivery might be in the order of two liters, which provides for a maximum delivery of 80 Grams of acetylated starch by this route, or indeed with a formulation having 5% that capacity will be raised to 100 grams per day. The stated requirement of fibre intake per day for a person is 30 grams (Baghurst et al Supplement to Food Australia 48(3) s3–s35, 1996). Of this fibre nearly all will reach the large bowel. If resistant starch was substituted for fibre here might be a loss during transit through the small intestine and it is estimated that to meet the recommended delivery one might need to provide 40 grams per day. It is noted however that the fatty acid delivery agent of the present nasogastric formulation need not necessarily provide 30 grams. Firstly it might not necessarily be the only component that provides the benefits of fibre, such as luminal hydration and faecal bulking, and secondly the capacity to deliver the health giving SCFA is enhanced because they are readily cleavable form the carrier. It might thus be feasible that a benefit be effected should 5 grams be delivered per day. Accordingly a formulation of 0.25% may give a health benefit. It would be noted however that such a low level is not preferred firstly because the tube fed delivery might only be one liter or even less, and secondly it will usually be desirable that the level of SCFA is somewhat higher. In particular where the individual receiving the feed has undergone short term trauma and it is desirable that the SCFA level be increased rapidly. Generally the lower levels might be desirable where the individual is tube fed for extended periods, and perhaps levels of about 0.5% to about 1.0% might be preferred, whereas for acute treatment higher levels such as from about 2% to about 4% might be desired. Where the degree of substitution of the acetylated starch is higher than the 0.25 of the preparation prepared there will be a capacity to introduce a higher level of the acylated starch. In the case of delivery of other fatty acids such as omega 3 fatty acids quite low levels may also give benefits.

It will be understood that enteral feed are also given to suffers of diarrhoeal conditions such as cholera, where up to about 4 liters of formulation are given, to compensate for fluid loss associated with the condition, and accordingly the level of fatty acid delivery agent within the formulation might be modified to suit such a rate of application. Similarly enteral formulations are also given to infants where the rate of administration is very low, and may be in the order of 100 ml. The 30 grams of fibre estimated by Baghurst et al (supra) is based on an adult's requirement and the requirement for an infant will be smaller than that, nevertheless a higher concentration may be needed in infant formulations.

Additionally it is anticipated that starch or resistant starches substituted with a similar degree of substitution with butyrate and propionate substitutions will also be able to be administered via a nasogastric tube at comparable levels.

It is anticipated that a solution with a viscosity of about 40cP at 25° C. will be able to be used through a feeding tube and accordingly this then enables a trial of various formulations of fatty acid delivery agents.

Example 8

Formulations

The formulations contemplated by this invention vary considerably in their application. As can be seen from the data above, formulations can give rise to increased SCFA in a matter of hours and therefore formulations can be for short term use especially for recovery from surgery, or the acute onset of a condition. Additionally the present invention might be used for delivery of SCFA where it is required that the individual be tube fed for longer periods of time, and accordingly encompasses the provision of a dry powder to which may be added water to make up the liquid formulation of the invention. Set out in the table below are a number of formulations the majority of which are devised for humans both for short and long term application, and to which fatty acid delivery agent can be added.

TABLE 13

Nasogastric Formulations

| Product Name | UCNF* | Nutrison energy | Nutrison multi fibre | Nutrison low sodium | Osmo-lite | En-sure |
|---|---|---|---|---|---|---|
| | | g per L | | | | |
| Protein | 67.8 | 60 | 40 | 40 | 37.2 | 37.2 |
| Lipid ## | 28.2 | 58 | 39 | 39 | 38.5 | 37.2 |
| Carbohydrate | | | | | | |
| Hydrolysed Starch | 161.2 | 140 | 94 | 94 | 110 | 110 |
| Sugar | 40.3 | 44 | 29 | 29 | 35 | 35 |
| Fibre | 19.89 | 0 | 15 | 0 | | |
| Gum arabic | 7.95 | | | | | |
| Fructooligo-saccharide | 7.95 | | | | | |
| Xylooligo-saccharides | 3.99 | | | | | |
| Vitamins | 1.4 | 0.3 | 0.3 | 0.3 | 0.51 | |
| Minerals | 9.0 | 4.8 | 4.8 | 4.8 | 3.8 | |
| Water | | 780 | 850 | 850 | 841 | 844 |
| Protein | 39.7 | 44.4 | 69.9 | 30 | 41.7 | 62.6 |
| Lipid ## | 37.2 | 36.8 | 95.6 | 49.7 | 10.8 | 9.1 |
| Carbohydrate | | | | | | |
| Hydrolysed Starch | 123 | 116 | 192.5 | 80.7 | 141 | 81 |
| Sugar | 39 | 36 | 22.7 | 29 | 44 | 25 |
| Fibre | 829 | 833 | 703 | 844 | 867 | 786 |

TABLE 13-continued

Nasogastric Formulations

| Product Name | UCNF* | Nutrison energy | Nutrison multi fibre | Nutrison low sodium | Osmo-lite | En-sure |
|---|---|---|---|---|---|---|
| Gum arabic | | | | | | |
| Fructooligo-saccharide | | | | | | |
| Xylooligo-saccharides | | | | | | |
| Vitamins | | | | | | |
| Minerals | | | | | | |
| Water | | | | | | |

*UCNF (Ulcerative Colitis Nasogastric Formula) is an experimental formulation for pigs.
Nutrison ™ products are available from Nutricia, Zoetermeer, Holland.
Nepro ™, Osmolite ™, Ensure ™, Jevity ™, Vital ™ and Pulmocare ™ are all nasogastric enteral preparations marketed by the Ross Products Division of Abbott Laboratories, Columbus, Ohio
3% of the lipid is in the form of lecithin.

The fatty acid delivery agent can be added to these formulations as simple additions or they may substitute existing components, especially where the fatty acid delivery agent is a substitute such as for the energy of the hydrolysed starch or sugar component. It is preferred that the fatty acid delivery agent be added during the manufacture of the entire formulation, however it might be desired to add an amount of the fatty acid delivery agent closer to the time of feeding.

The fatty acid delivery agent might be an acetylated resistant starch where the acetylation is made according to an aqueous method such as by the method of example 6. This could be added to any one of the formulations set out in Table 11, simply by addition of dry powder, mixing and dissolving, followed by sterilisation by autoclaving. The addition may be at a rate of between 0.5% to about 5% w/v, but it is anticipated that it is likely to be about 2%. Care will be taken not to freeze the preparation because that may have an adverse effect on the substituted starch, and interferes with the process, and a result is that there is no significant increase in release of SCFA into the large bowel, perhaps as a result of the integrity of the preparation being compromised. It is also known that if a DMSO based method of acylation is used then the efficacy of the preparation is also diminished because of an increased viscosity so that only much lower levels of the substituted starch can be solubilised in the nasogastric preparation.

The acetylated starch is thought likely to be a constituent of both the aqueous phase and the lipid phase of the preparation, and that may account for its observed capacity to stabilise the emulsion.

An alternative example of a nasogastric formulation is a fatty acid substituted fructo-oligosaccharide. Such smaller polar molecules are likely to only be incorporated into the aqueous phase.

The composition of the formulation can be vary as known in the making of such formulations, the addition of the fatty acid delivery agent at levels that give a detectable increase in the amount of the fatty acid in the large bowel.

The SCFA that are considered to be most beneficial in treatment or prevention of certain colonic disorders are those fatty acids with carbon chain lengths of 2, 3 and 4, namely acetate, propionate, and butyrate. However other SCFA may also have beneficial effects and therefore the term SCFA includes branched chain or substituted short chain fatty acids. There is doubt as to whether formate (C1) is of benefit in adults but may be of benefit in children (Bird et al. *Curr Issues Intest Microbiol* (2000) 1(1):25–37). SCFA of other lengths may also be may also be beneficial so that the term SCFA is to be understood to include those fatty acids with a chain length in the range of between and including 1 to 6 carbons, and accordingly caproic and valerate and isovalerate are included in that description. It is also to be understood that fatty acids with longer carbon chain lengths may also be beneficial and may be covalently bonded to a carrier in a similar fashion. The fatty acids envisioned by this invention are all susceptible to breakdown before arriving at the colon, unless protected.

Other fatty acids that might also be contemplated by this invention might include omega-3 polyunsaturated fatty acids such as linolenic acid (18:2), eicosapentaenoic acid (20:5), docosahexaenoic acid (22:6), and stearadonic acid. The fatty acid delivery agent might include substitution by more than one fatty acid, or class of fatty acid.

The carrier to which the SCFA is bonded is preferably a carbohydrate, although other carriers may also be used. Using a carbohydrate has several advantages, largely because of the availability of carbohydrates in commercial quantities and because the effects of carbohydrates in the alimentary tract are relatively well understood. Some forms of carrier are undesirable, for example protein is undesirable because after fermentation of the protein by products are formed that have an adverse effect on the colon.

Several forms of carbohydrate may be used as a carrier, these may include soluble non-starch polysaccharides, insoluble non-starch polysaccharides and oligosaccharides. The carbohydrates used may include but are not limited to pectins, gums and mucilages, celluloses, hemicelluloses, gums, inulin, oligosaccharides and glucans.

Any suitable source of pectin may be used and the following are illustrative of the types that might be used: —High, medium and low methoxylated pectins, high, medium and low gel strength pectins. The pectin may be derived from any number of sources which sources may include from apples, oranges and lemons.

Any suitable source of gums may be used and the following are illustrative of the types that could be used:—guar, xanthan, arabic, tragacanth, locust bean and psyllium. Modified and artificial gums may also act as a carrier.

The soluble non-starch polysaccharides may include long chain inulin, pectin, chitin, β glucans, mucilages, agar, carageenans, alginates and similar. Most of these soluble fibres are fermentable for the largest part.

The insoluble non-starch polysaccharides may include cellulose (for example derived from oat hull, soybeans, cereal bran) and hemicellulose (mostly branched arabinoxylans or galactans, for example from cereals, potatoes or soybeans). Other celluloses may be used include, but are not limited to, microcrystalline and other chemically modified celluloses.

Oligosaccharides are understood to comprise any saccharide containing at least two and up to 10 monosaccharide units, whether of starch ($\alpha$ glucan) or non-starch type. Examples of oligosaccharides that might be used as carriers include fructo- and galacto-oligosaccharides such as hydrolysed inulin and levan (fructans), and short chain amylodextrins, malto dextrins and modifications and derivatives thereof.

The use of simple sugars such as glucose, fructose, galactose, sucrose and lactose, is limited because these may result in osmotic effects that lead to diarrhoea if administered at levels that are too high, however, it may be possible to use these in dilute solutions to effect an improvement in SCFA delivery.

One of the preferred forms of carrier is a starch because it can be fermented by microorganisms in the colon, and accordingly provides for extra nutrients for bacterial bulking in the colon, as well as separately providing a further source of SCFA additional to the SCFA linked to the carrier. Furthermore starch is readily available commercially.

The starch may be a starch that is digestible in the small intestine. Such digestible starch is protected to some extent from the degrading effects of $\alpha$ amylases in the small intestine by the SCFA. The extent that the starch is protected will depend upon the degree of substitution, and if there is only a relatively low degree of substitution, then the starch will rapidly be degraded and there will be relatively good access by the low levels of esterases that exist in the upper alimentary tract to the ester bonds to cleave many of the SCFAs from the carrier thereby leading to ineffective delivery to the colon. It may therefore be advantageous to use a resistant starch that is already resistant to digestion in the small intestine, but that is digestible in the colon. This will maximize the delivery of starch, and probably SCFA.

The term starch is understood to include all forms of starch including modified starches, and the modification can be physically, enzymically, esterification, oxidation acid cleavage, and reaction with difunctional reagents, and includes those forms of starch that might be included in the classification RS1, RS2. RS3 and RS4. Starch can be derived from a great many sources, and may be derived, for example, be native starches from wheat, potato, tapioca, maize, rice and oats. The carrier may be a resistant starch which resists digestion because of its physical size, granular nature or starch type (e.g. high amylose maize). Such starch includes those found in potato, green banana and legumes such as peas and may occur additionally due to retrogradation following heat treatment causing granular disruption, hydration and subsequent reassociation in an enzymatic resistant form.

A high amylose starch is in one form a preferred carrier, because the acylation need not necessarily protect the carrier from digestion in the small intestine and because resistant starch carried through to the large bowel is known to be a particularly good substrate for colonic fermentation. Such a high amylose starch can be a quite high amylose starch having perhaps greater than 60% amylose or more preferably higher than 80% amylose. Examples of such starches are those available from Goodman Fielder Melbourne, Australia under the name Hi Maize™.

It is to be understood that the carbohydrates listed may be modified, either singly or multiply though the use of:—
heat and/or moisture
physical treatment (e.g. ball milling)
enzymatic treatment (e.g. $\alpha$ or $\beta$ amylase, pullulanase or the like)
chemical hydrolysis (wet or dry using liquid or gaseous reagents)
esterification (eg chemical with propylene oxide)
oxidation
cross bonding with difunctional reagents (e.g. sodium trimetaphosphate, phosphorous oxychloride)
carboxymethylation or other forms of modification known to those practiced in the art. These can occur in aqueous and nonaqueous environments. This list of modifications is not intended to be exhaustive or limiting.

Where it is desired to deliver only one SCFA then a non-digestible carrier, i.e. one that is not degraded by bacterial enzymes of the colon is preferably used, leading to more accurate control over delivery of a single SCFA, and this may have beneficial effects on the treatment or prevention of certain disorders. The degree of substitution coupled with the quantity of the agent ingested can be used to regulate the level of one or more SCFA delivered to the colon.

The invention is beneficial in the maintenance of visceral health in adults children and infants, and includes the method of reducing the risk of any one or more one of the gastrointestinal disorders selected from the following; cancer, constipation, diverticulitis, colitis and irritable bowel and infectious conditions such as diarrhoea and includes the steps of orally taking an effective dose of the agent according to this invention at regular intervals. Additionally the invention might include a method for recovery from a medical treatment, the treatment resulting in an injury to the large bowel, such as surgery or treatment of a bowel cancer such as by chemotherapy.

The daily dosage rate for a SCFA substituted onto a resistant starch such as a resistant maize starch at a degree of substitution of 0.25 may be in the range of about 5 to 80 grams per day although other dosage rates may be employed, and perhaps most preferably about 40 grams per day. It would be expected that similar dosages rates would be appropriate for other forms of the agent.

It is to be understood that this invention also has application to both animals as well as humans and accordingly the SCFA substituted carrier can be used either in the treatment of animal colonic disorders or in the prevention of colonic disorders and may therefore be included in various forms of pet formulation or food for animals of commercial importance such as pigs and horses.

The bond between the fatty acid and the carrier is one that can be cleaved by an agent in the bowel to give free fatty acid which can then be absorbed. It is to be understood that the cleavage can be either by a single enzyme, or may take a second step where that enzyme is present in or around the colon.

The bond between the fatty acid and the carrier is preferably an ester bond, because the capacity of the microbial flora of the large bowel to hydrolyse ester bonds is far greater than is the capacity of other portions of the alimentary tract to do so. Furthermore because hydroxyl groups are generally abundant amongst many carbohydrates there is a potential for a large range of densities of substitution and the ability to substitute is relatively easy.

Other forms of bonding may include amide bond to amino sugars, however such sugars are relatively rare in unmodified carbohydrates, and the rarity limits the extent of substitutions that might be made, or alternatively limits the usefulness to modified carbohydrates, some of which might have other specific advantages. Alternatively the link may be different where substituted fatty acids are used.

It might also be desired to add further components for example specific vitamins, minerals water and fat soluble anti-oxidants and additional pharmaceutical therapeutics or additives.

The degree of substitution can depend on the desired outcome, and degree of bulk or bacterial build-up that is desired. For example where a SCFA is bonded to a carbohydrate it is considered unlikely that the esterases will be able to access the ester bond between the sugar moiety and the SCFA moiety if more than one SCFA is present per carrier residue molecule. Furthermore it is likely that the surface characteristics of the carbohydrate will be modified to an extent that the carbohydrate will no longer be water soluble. In one form it is preferred that the degree of substitution be less than one per sugar moiety. However in another form it might be desired that the fatty acid delivery agent is soluble in the lipid phase of the nasogastric feed, and higher degrees of substitution might be acceptable than where the fatty acid delivery agent was to have been water soluble.

The term degree of substitution, as will be understood, not to imply that each carrier molecule is evenly or equally substituted, but is to be taken as meaning an average degree of substitution. As in most substitution reactions, product molecules with a range of substitutions will result.

Where a digestible starch is used it is considered unlikely that any significant protection to cleavage will result if less than one SCFA is bonded for every twenty sugar molecules, accordingly in a preferred form of the first aspect of the invention the degree of substitution is selected from within the range of 0.05 to 1 SCFA per sugar moiety. Generally however for ease of synthesis and handling a range of between about 0.1 and 0.5 is convenient. Other carbohydrates however are able still to be handled and solubilized where the degree of substitution is greater than one and therefore generally the degree of substitution is selected from the range of 0.05 to 2, and perhaps most conveniently is 0.25.

One of the major limitations of providing a source of SCFA for delivery enterally is that free fatty acids are readily degraded before reaching the colon. Other sources of SCFA such as resistant starches can be delivered only in diminished quantities or in quantities that are not fully controllable such as where the resistant starches sediment because the granular nature of the resistant starch particles. Additionally, and especially in the case of naive recipient such as are often the case in patients requiring nasogastric enteral feed, the presence of a bacterial population capable of giving a high level of SCFA is not necessarily always present, whereas enzymes capable of cleaving the typical ether or ester bonds are far more pervasively present.

Thus where a hopitalised patient who for example requires surgery to address colon cancer, and who has had antibiotic treatment, the microflora will be considerably compromised. The delivery of a nasogastric formulation of at least some embodiments of this invention can provide for an increased amount of SCFA within the colon in the short space of time of a few hours giving the known benefits for recovery that such SCFAs have.

What is claimed is:

1. An enteral formulation for nasogastric delivery comprising:
   a) an amino acid source,
   b) a carbohydrate source,
   c) a lipid source, and
   d) a fatty acid delivery agent, being a fatty acid covalently bonded to a carrier molecule by a bond hydrolysable in the colon to thereby release the fatty acid, the covalent bonding providing a protective effect to both the carrier and fatty acid from degradation in the stomach or small intestine, said carrier being any one of a starch, a non-starch polysaccharide, or oligosaccharide the fatty acid delivery agent being present in the formulation range of 0.25% w/v through to 5% w/v, and wherein the formulation can be delivered through an enteral feeding tube.

2. An enteral formulation for nasogastric delivery as in claim 1 wherein the formulation is capable of being stored for at least 24 hours and not forming a gel viscous solution or precipitate that is not easily resuspended.

3. An enteral formulation for nasogastric delivery as in claim 1 wherein the enteral formulation is also an elemental formulation and includes a mineral source and a vitamin source.

4. An enteral formulation for nasogastric delivery as in claim 1 wherein the fatty acid is a short chain fatty acid (SCFA).

5. An enteral formulation for nasogastric delivery as in claim 4 wherein the SCFA comprises a carbon chain length between 1 and 10.

6. An enteral formulation for nasogastric delivery as in claim 4 wherein the SCFA comprises a chain length between 2 and 4.

7. An enteral formulation for nasogastric delivery as in claim 1 wherein the fatty acid is a SCFA or an omega 3 fatty acid, an omega 6 fatty acid or stearadonic acid.

8. An enteral formulation for nasogastric delivery as in claim 7 wherein the omega 3 fatty acid is selected from the group consisting of linolenic acid, eicosapentaenoic acid, and docosahexaenoic acid, and the omega 6 fatty acid is linoleic acid.

9. An enteral formulation for nasogastric delivery as in claim 1 wherein the carrier is a non-starch polysaccharide or oligosaccharide.

10. An enteral formulation for nasogastric delivery as in claim 9 wherein the non-starch polysaccharide is selected from the group consisting of inulin, chitin, β glucans, mucilages, agar, carageenans and gums including guar, arabic, xanthan, tragacanth, locust bean and psyllium.

11. An enteral formulation for nasogastric delivery as in claim 4 wherein the carbohydrate is a starch.

12. An enteral formulation for nasogastric delivery as in claim 11 wherein the starch is a starch digestible in the small intestine.

13. An enteral formulation for nasogastric delivery as in claim 11 wherein the starch is a starch resistant to digestion in the small intestine.

14. An enteral formulation for nasogastric delivery as in claim 13 wherein the starch is a high amylose starch.

15. An enteral formulation for nasogastric delivery as in claim 11 wherein the starch is a modified starch.

16. An enteral formulation for nasogastric delivery as in claim 15 wherein the starch is modified through the use of any one or more of the following, heat and/or moisture, physically, enzymatically, chemical hydrolysis, esterification, oxidation, cross bonding with difunctional reagents, and carboxymethylation.

17. An enteral formulation for nasogastric delivery as in claim 1 wherein the bond is selected from the group consisting of a ester bond, an ether bond or an amide bond.

18. An enteral formulation for nasogastric delivery as in claim 11 wherein the the carbohydrate has a degree of substitution ranges from 0.05 acyl group per saccharide unit to 2 acyl groups per saccharide unit.

19. An enteral formulation for nasogastric delivery as in claim 11 wherein the the carbohydrate has a degree of substitution ranges from 0.1 acyl groups per saccharide unit to 0.5 acyl group per saccharide unit.

20. An enteral formulation for nasogastric delivery as in claim 4 wherein the carrier is a starch and the formulation having by weight 0.25% to about 5% of the fatty acid delivery agent.

21. An enteral formulation for nasogastric delivery as in claim 4 wherein the carrier is a starch and the formulation having by weight 0.5% to about 4% of the fatty acid delivery agent.

22. An enteral formulation for nasogastric delivery as in claim 4 wherein the carrier is a starch and the formulation having by weight about 2% of the fatty acid delivery agent.

23. A method of elevating the level of a fatty acid in the colon of a human or animal, including the step of delivering a fatty acid delivery agent in a physiologically acceptable medium through a feeding tube to elevate the level of the fatty acid, the fatty acid delivery agent being a fatty acid covalently bonded to a carrier molecule by a bond hydrolysable in the colon to thereby release the fatty acid, the covalent bonding providing a protective effect to both the carrier and fatty acid from degradation in the stomach or small intestine, said carrier being a starch, a non-starch polysaccharide or an oligosaccharide, the fatty acid delivery agent being present in the formulation range of 0.25% w/v through the 5% w/v.

24. The method of claim 23 wherein the physiological acceptable medium is an enteral feed formulation, including,
    a) an amino acid sequence,
    b) a carbohydrate source, and
    c) a lipid source.

25. The method of claim 23 wherein the fatty acid is a SCFA.

26. The method of claim 25 wherein the carrier is a starch.

27. The method of claim 23 wherein the level of the fatty acid within the large bowel is elevated within a time period of 6 hrs.

28. The method of claim 25 wherein the level of the SCFA within the large bowel is elevated within a time period of 4 hrs.

29. The method of claim 25 wherein the level of the SCFA within the large bowel is elevated within a time period of 2 hrs.

30. The method of claim 26 wherein the enteral formulation is delivered through a nasogastric tube.

31. The method of claim 26 wherein the starch is a resistant starch.

32. The method of claim 31 wherein the resistant starch is a high amylose starch.

33. The method of claim 32 wherein the SCFA is selected from the group consisting of acetate, propionate and butyrate.

34. The method of claim 33 wherein the quantity of fatty acid delivery agent delivered is between 5 and 80 gm/day.

35. The method of claim 33 wherein the quantity of fatty acid delivery agent delivered is between about 10 and 60 gm/day.

36. The method of claim 33 wherein the quantity of fatty acid delivery agent delivered is between about 40 gm/day.

37. The method of claim 34 wherein no more than 2 litres of the enteral formulation is delivered within a 24 hour time period.

38. The method of claim 34 wherein no more than 1 liter of the enteral formulation is delivered within a 24 hour time period.

39. The method of claim 34 wherein the fatty acid delivery agent is present in the formulation at about 2% by weight of the formulation.

40. An enteral formulation for nasogastric delivery as in claim 1 wherein
    the carrier molecule is selected from the group consisting of a non-starch polysaccharide and/or oligosaccharide:

the non-starch polysaccharide being selected from the group consisting of inulin, chitin, β-glucans, mucilages, agar, carageenans, gums, cellulose, and hemicellulose, or the gum being selected from the group consisting of guar, arabic, xanthan, tragacanth, locust bean and psyllium, or the cellulose being selected from the group of celluloses derived from oat hullo, soybeans and cereal bran, microcrystalline celluloses, methyl celluloses, hydroxypropylmethyl cellulose and carboxymethylcellulose, or the oligosaccharide being selected from the group consisting of fructooligosacchardies, galactooligosaccharides, short chain amylodextrins and maltodextrins and modifications and derivatives thereof.

41. The formulation of claim 1 wherein the viscosity of the formulation at 25° C. is no greater than 40cP.

42. The formulation of claim 1 wherein The polysaccharide is fermentable in the colon.

43. The method of claim 23 wherein the physiological acceptable medium is water.

44. The method of claim 23 wherein the level of fatty acid within the large bowel is elevated within a time period of about 1 hour.

45. The method of claim 23 wherein the human or animal suffers from a gastrointestinal condition and said elevation in level is rapid in relation to an increase in fatty acid levels due to fermentation of ingested carbohydrate so that at least one of the effects of said condition are ameliorated rapidly after administration.

46. The method of claim 45 wherein the condition is an acute condition in which increased levels of fatty acid are beneficial and levels of the fatty acid need to be increased within tree hours of delivery of the fatty acid delivery agent to a pan of the bowel.

47. The method of claim 45 wherein the concentration of fatty acid delivery agent is greater than 1% w/v.

48. The method of claim 23 wherein the fatty acid is a short chain fatty acid (SCFA).

49. The method of claim 48 wherein the SCFA comprises a carbon chain length between 1 and 10.

50. The method of claim 48 wherein the SCFA comprises a carbon chain length between 2 and 4.

51. The method of claim 47 wherein the condition is selected from the group consisting of diarrhea, post operable surgery, gastrointestinal bacterial infections, antibiotic treatment chemotherapy and radiotherapy treatments.

52. The method of claim 26 wherein the starch is a modified starch.

53. The method of claim 52, wherein the starch is modified through the use of any one or more of the following, heat and/or moisture physically, enzymatically, chemical hydrolysis, esterification, oxidation, cross bonding with difunctional reagents, and carboxymethylation.

* * * * *